United States Patent [19]

Leunbach

[11] Patent Number: 5,231,354
[45] Date of Patent: Jul. 27, 1993

[54] MAGNETIC RESONANCE IMAGING
[75] Inventor: Ib Leunbach, Dragör, Denmark
[73] Assignee: Nycomed Innovation AB, Malmo, Sweden
[21] Appl. No.: 635,150
[22] PCT Filed: Jul. 25, 1998
[86] PCT No.: PCT/EP89/00874
 § 371 Date: Jan. 16, 1991
 § 102(e) Date: Jan. 16, 1991
[87] PCT Pub. No.: WO90/02345
 PCT Pub. Date: Mar. 8, 1990
[30] Foreign Application Priority Data
 Aug. 19, 1988 [GB] United Kingdom ............... 8819753
[51] Int. Cl.⁵ .................................. G01R 33/20
[52] U.S. Cl. ................................... 324/316
[58] Field of Search ............ 324/300, 301, 304, 307, 324/309, 318, 322; 128/653.5

[56] References Cited

U.S. PATENT DOCUMENTS

| | | | |
|---|---|---|---|
| 3,966,409 | 6/1976 | Hrvoic et al. | 23/230 R |
| 4,615,879 | 10/1986 | Runge et al. | 128/653 |
| 4,683,433 | 7/1987 | Yamamoto et al. | 324/309 |
| 4,719,425 | 1/1988 | Ettinger | 324/316 |
| 4,777,957 | 10/1988 | Wehrli et al. | 128/653 |
| 5,051,698 | 9/1991 | Ordidge | 324/309 |
| 5,111,819 | 5/1992 | Hurd | 324/309 |

FOREIGN PATENT DOCUMENTS

| | | |
|---|---|---|
| 0071564 | 2/1983 | European Pat. Off. |
| 0296833 | 12/1988 | European Pat. Off. |
| 0302742 | 2/1989 | European Pat. Off. |
| WO85/02772 | 7/1985 | PCT Int'l Appl. |
| WO85/04330 | 10/1985 | PCT Int'l Appl. |
| WO90/00904 | 2/1990 | PCT Int'l Appl. |

OTHER PUBLICATIONS

Lurie et al, *Journal of Magnetic Resonance*, 76, 1988, No. 2, 366–370.

*Primary Examiner*—Michael J. Tokar
*Attorney, Agent, or Firm*—Bacon & Thomas

[57] ABSTRACT

The present invention describes a method of and apparatus for performing electron spin resonance enhanced magnetic resonance imaging (ESREMRI) at ultra-low fields of up to 20 Gauss, optionally dispensing with a primary magnet and using the earth's ambient field to provide the primary magnetic field for the magnetic resonance imaging procedure.

25 Claims, 2 Drawing Sheets

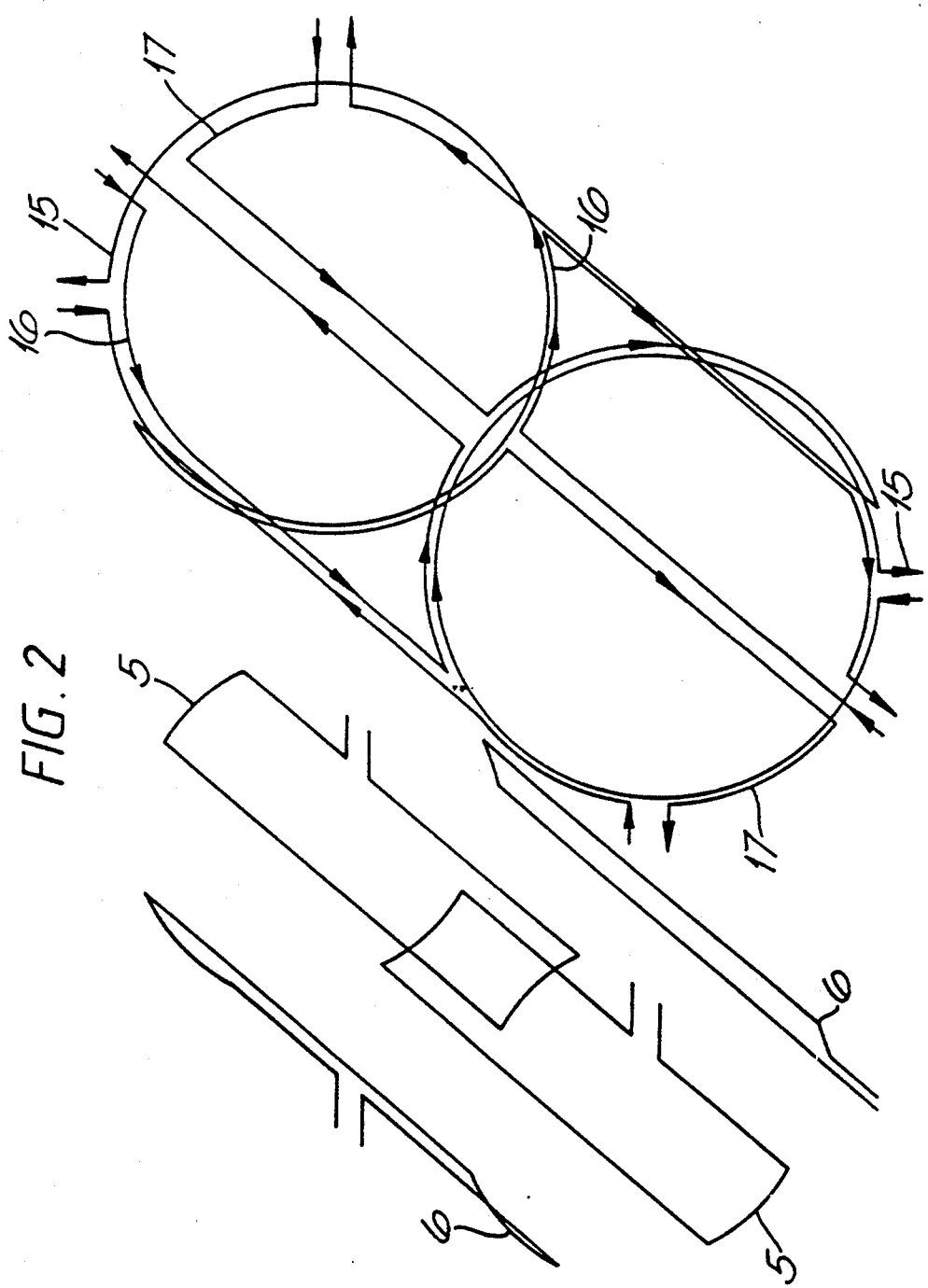

MAGNETIC RESONANCE IMAGING

The present invention relates to improvements in and relating to magnetic resonance imaging (MRI) apparatus and methods, and in particular to apparatus and methods for diagnostic imaging or mass screening and to contrast agents and media for use in such methods.

MRI is a diagnostic technique that has become particularly attractive to physicians as it is non-invasive and does not involve exposing the patient under study to potentially harmful radiation such as the gamma-radiation or X-radiation of conventional radiographic imaging.

Conventional MRI apparatus however is exremely costly to manufacture and operate and accordingly the occurence of MRI apparatus in hospitals, clinics and other medical or research institutions has thus far been relatively limited.

The expense of manufacture and operation of MRI apparatus is closely associated with the field strength that the primary magnet in the apparatus is required to generate in order to produce images of acceptable spatial resolution within an acceptable image acquisition time.

In general, primary magnets capable of generating field strengths of 0.1 to 2 T have been used and image acquisition times have been of the order of 10 to 30 minutes.

For relatively low field strengths of up to 0.15 T, resistive magnets (generally adjacent coaxial metal coils) have been used but the energy requirement (and as a result the heat generation) of such resistive magnets is very high. Thus a 0.1 T magnet will require about 30 kW electric power. For higher fields, superconducting magnets are conventionally used. The selection of the appropriate magnetic field strength involves balancing various factors: thus higher field results in a better signal/noise (S/N) ratio and hence better spatial resolution at a given S/N value, but also in greater manufacturing and operating expense and in poorer tissue contrast.

There is therefore a demand for MRI apparatus and techniques capable of achieving acceptable or improved in S/N ratios but using lower field magnets and without undue loss in spatial resolution.

The present invention is based on the concept of dispensing with the primary magnet and using as the constant field the earth's magnetic field. The extreme weakness of this field is a potential disadvantage which has deterred proposals for this approach until now but the ESREMRI technique which is described in detail hereinafter enables that weakness to be overcome.

The long image acquisition times generally result from the need to perform a large number (e.g. 64-1024) of pulse and detection sequences in order to generate a single image and in the need to allow the sample under study to reequilibrate between each sequence.

The degeneracy of the spin states of nuclei with non-zero spin, e.g. $^1H$, $^{13}C$, $^{19}F$, etc., is lost when such nuclei are placed within a magnetic field and transitions between the ground and excited spin states can be excited by the application of radiation of the frequency ($\omega_o$) corresponding to energy difference E of the transition (i.e. $\tau\omega_o = E$). This frequency is termed the Larmor frequency and is proportional to the strength of the field experienced by the nucleus. As there is an energy difference between the spin states, when the spin system is at equilibrium the population distribution between ground and excited spin states is a Boltzmann distribution and there is a relative overpopulation of the ground state resulting in the spin system as a whole possessing a net magnetic moment in the field direction. This is referred to as a longitudinal magnetization. At equilibrium the components of the magnetic moments of the individual non-zero spin nuclei in the plane perpendicular to the field direction are randomized and the spin system as a whole has no net magnetic moment in this plane, i.e. it has no tranverse magnetization.

If the spin system is then exposed to a relatively low intensity oscillating magnetic field perpendicular to the main field and produced by radiation at the Larmor frequency, transitions between ground and excited spin states occur. If the exposure is for a relatively short duration then the resultant magnitudes of the longitudinal and transverse magnetizations of the spin system are functions of the exposure duration which oscillate about zero at the Larmor frequency and are 90° out of phase with each other. Thus, from equilibrium, a pulse of duration $(2n+1)\pi/2\omega_o$ (a so-called 90° pulse when n is even and a 270° pulse when n is odd) leaves the system with maximum transverse magnetization (of magnitude proportional to the initial longitudinal magnetization at equilibrium) and no longitudinal magnetization, a pulse of duration $(2n+1)\pi/\omega_o$ (a 180° pulse) leaves the system with inverted longitudinal magnetization and inverted transverse magnetization (and hence from equilibrium no transverse magnetization), etc.

When the pulse is terminated, the oscillating magnetic field produced by any resulting net transverse magnetization can induce an oscillating electrical signal (of angular frequency $\omega_o$) in a detector coil having its axis arranged perpendicular to the main field direction. For this purpose the transmitter used to emit the pulse can also be used as a detector.

Induced nuclear magnetic resonance signals, hereinafter termed free induction decay (FID) signals, have an amplitude proportional to the transverse magnetization (and hence generally to the original population difference between ground and excited spin states).

If the nuclei of the spin system experienced an entirely uniform magnetic field, the FID signal would decay due to spin-spin interactions at a rate with a characteristic time of $T_2$, the transverse or spin-spin relaxation time. However, due to local field inhomogeneities, the nuclei within the spin system will have a spread of Larmor frequencies and decay of transverse magnetization is more rapid, having a characteristic time of $T_2^*$ where $1/T_2^* = 1/T_2 + 1/T_{inh}$, $T_{inh}$ representing the contribution due to field inhomogeneities. This contribution is proportional to the uniform magnetic field. $T_2$ itself can be determined using spin-echo imaging in which, after the decay of the FID signal (usually following a 90° pulse) the system is exposed to a 180° pulse and an "echo" signal is generated, the decay in the amplitude of the echo being governed primarily by $T_2$ as, with the inversion of the transverse magnetization for the individual nuclei, the field inhomogeneities referred to above cause tranverse magnetization to build up to a maximum at time TE/2 after the 180° pulse where the time between the previous maximum transverse magnetization and the 180° pulse is also TE/2.

To generate different images, different pulse and FID detection sequences are used. Perhaps the simplest is saturation recovery (SR) where the FID signal is determined after a single 90° initiating pulse. The signal strength is dependent upon the magnitude of the longitudinal magnetization before the pulse, and hence on the nuclear density and the extent to which the system reequilibrates in the time (TR) between successive initiating pulses. In spin-echo imaging, for example multiple-echo imaging, the pulse and detection sequence may be: initiating 90° pulse (at time 0), FID detection (following the initiating pulse), 180° pulse (at time TE/2), detection of 1st echo (at time TE), 180° pulse (at time 3TE/2), detection of 2nd echo (at time 2TE) . . . , initiating pulse for the next sequence (at time TR), etc. In this technique, a TR is selected which is sufficient for a reasonable reequilibration to occur in the period between successive initiating pulses.

As is explained further below in connection with the example of two dimensional Fourier transformation (2DFT) image generation, in order to generate a single image with adequate spatial resolution, it is necessary to perform a large number (e.g. 64–1024) of separate pulse and detection sequences. Since TR has in principle to be large with respect to $T_1$, the characteristic time for relaxation of the excited system towards the equilibrium Boltzmann distribution between ground and excited spin states, to permit longitudinal magnetization to build up between successive pulse sequences so as to avoid the FID signal strength decaying in successive pulse sequences, the total image acquisition time is generally relatively large. Thus, for example, TR may conventionally be of the order of seconds and the image acquisition time may be of the order of 10–30 minutes.

Certain so-called fast imaging (FI) techniques may be used to accelerate reequilibration and so reduce image acquisition time; however they inherently result in a reduction in the S/N ratio and/or contrast and hence in poorer image quality. The FI technique involves for example exciting the spin system with a less than 90° pulse and thus the difference between ground and excited spin state populations is only reduced rather than eliminated (as with a 90° pulse) or inverted and so reattainment of equilibrium is more rapid. Nevertheless, the transverse magnetization generated by the less than 90° pulse is less than that for a 90° pulse and so FID signal strength and thus S/N ratio and the spatial resolution in the final image are reduced.

The long image acquisition time in conventional MRI thus significantly detracts from the attractiveness of MRI for mass or routine diagnostics screening and for all forms of diagnostic imaging where it is necessary to build up a three-dimensional image by imaging successive adjacent sections through the patient.

A further problem in MRI, that of achieving adequate image contrast between different tissue types having the same or closely similar image parameters, e.g. to cause a tissue abnormality to show up clearly in the magnetic resonance (MR) images, has been addressed in a variety of ways. Using different pulse and detection sequences and by manipulation of the acquired data, MRI can be used to generate a variety of different images, for example saturation recovery (SR), inversion recovery (IR), spin echo (SE), nuclear (usually proton) density, longitudinal relaxation time ($T_1$) and transverse relaxation time ($T_2$) images. Tissues or tissue abnormalities that have poor contrast in one such image often have improved contrast in another. Alternatively, imaging parameters (nuclear density, $T_1$ and $T_2$) for tissues of interest may be altered by administration of a contrast agent. Thus many proposals have been made for the administration of magnetically responsive materials to patients under study (see for example EP-A-71564 (Schering), U.S. Pat. No. 4,615,879 (Runge), WO-A-85/02772 (Schröder) and WO-A-85/04330 (Jacobsen)). Where such materials, generally referred to as MRI contrast agents, are paramagnetic (for example gadolinium oxalate as suggested by Runge) they produce a significant reduction in the $T_1$ of the water protons in the zones into which they are administered or at which they congregate, and where the materials are ferromagnetic or superparamagnetic (e.g. as suggested by Schröder and Jacobsen) they produce a significant reduction in the $T_2$ of the water protons, in either case resulting in enhanced (positive or negative) contrast in the magnetic resonance images of such zones.

The contrast enhancement achievable by such agents is limited by a number of factors. Thus such contrast agents cannot move the MRI signal intensity ($I_s$) for any tissue beyond the maximum ($I_l$) and minimum ($I_o$) intensities achievable for that tissue using the same imaging technique (e.g. IR, SR, SE, etc.) in the absence of the contrast agent; thus if "contrast effect" is defined as $(I_s-I_o)/(I_l-I_o)$, contrast agents can serve to alter the "contrast effect" of a tissue within the range of 0–1. However to achieve contrast improvement an adequate quantity of the contrast agent must be administered to the subject, either directly to the body site of interest or in such a way that the natural operation of the body will bring the contrast agent to that body site.

Utilisation of the spin transition coupling phenomenon known in conventional nmr spectroscopy as the Overhauser effect to amplify the population difference between ground and excited nuclear spin states of the nuclear spin system producing the MR image by exciting a coupled esr transition in a paramagnetic species in the sample being imaged, generally a human or animal subject, has been proposed by us in EP-A-296833.

Our new technique for generating a magnetic resonance image of a sample, hereinafter termed Electron Spin Resonance Enhanced Magnetic Resonance Imaging or ESREMRI comprises exposing the sample to pulses of a first radiation of a frequency selected to excite nuclear spin transitions in selected nuclei in the sample and detecting free induction decay signals from the sample and is characterised in that it further comprises exposing the sample to a second radiation of a frequency selected to excite electron spin transitions coupled to nuclear spin transitions of at least some of the said nuclei.

The MRI apparatus for use in this technique requires a second radiation source for generating the radiation capable of stimulating such an esr transition as well as the first radiation source for generating the radiation used to stimulate the nuclear spin transition.

Thus in EP-A-296833 it was explained that, using ESREMRI, MR images having adequate signal to noise ratios, adequate spatial resolution and adequate image acquisition times could be produced using MRI apparatus provided with primary magnets generating primary fields of strengths around 200 G, well below those required for conventional MRI apparatus, that is primary magnets which would be significantly cheaper to construct and operate than those of conventional MRI apparatus.

Although EP-A-296833 refers to fields preferably in the range 20–1000 G and even the use of magnets to generate fields as low as the ambient field, about 0.5 G, it is not suggested that the ambient field itself could be used nor indeed is it explained how very low fields could give adequate FID signal strengths with an adequate signal/noise ratio, nor is it recommended, in fact, that fields below 20 G would have an advantage.

We have now realised that with appropriate choice of the material whose esr transition is stimulated by the second radiation the need for any primary magnet in ESREMRI apparatus may be avoided, the primary field of the apparatus being provided by the earth's ambient magnetic field. Alternatively, the earth's magnetic field may be magnetically balanced out and replaced by a further low-strength magnetic field e.g. up to 20 G. EP-A-296833 while allowing for fields below 20 G did not disclose the concept of balancing out the earth's field. It will be appreciated that the earth's field is at an angle of declination which is inconvenient for use as the uniform field in ESREMRI and this angle and the ambient field strength vary from place to place, thus requiring means for varying the RF and MW frequencies used and tomographically slicing the body under examination at an inconvenient angle to the horizontal.

The theoretical maximum image intensity enhancement, i.e. contrast effect, achievable using ESREMRI appeared to be approximately proportional to the ratio of the gyromagnetic constants for the electron and the resonating nuclei, e.g. about 330 for $^1$H MRI and indeed measured contrast effects of up to about 140 are quoted in EP-A-296833 for experiments performed using a primary magnetic field of 200 G. However, using fields not greater than 20 G, such as the ambient magnetic field, as explained below, still further enhancement is possible which partly offsets the reduction in signal strength due to the low field.

Thus viewed from one aspect the present invention provides an ESREMRI apparatus having a first radiation source capable of emitting a first radiation of a frequency selected to excite nuclear spin transitions in selected nuclei in a sample being imaged, a second radiation source capable of emitting a second radiation of a frequency selected to excite electron spin transitions coupled to the nuclear spin transitions of at least some of said selected nuclei, means for exposing said sample to a magnetic field gradient imposed on a uniform magnetic field and means for detecting free induction decay signals from said selected nuclei during the imposition of a said magnetic field gradient, characterised in that said first and second radiation sources are arranged to emit radiations of frequencies selected to excite said transitions using as the uniform magnetic field the ambient magnetic field or a magnetic field being a uniform field not greater than 20 G optionally and preferably combined with a field exactly balancing the earth's magnetic field.

Viewed from another aspect the invention provides an ESREMRI apparatus having a first radiation source capable of emitting a first radiation of a frequency selected to excite nuclear spin transitions in selected nuclei in a sample being imaged, a second radiation source capable of emitting a second radiation of a frequency selected to excite electron spin transitions coupled to the nuclear spin transitions of at least some of said selected nuclei, means for imposing a magnetic field gradient upon said sample and means for detecting free induction decay signals from said related nuclei during the imposition of a said magnetic field gradient, characterised in that said apparatus comprises either no uniform field generating magnet means or means for generating a uniform magnetic field of not greater than 20 G optionally but preferably together with means for balancing the earth's field.

In the apparatus of the invention where the earth's magnetic field at the sample is to be cancelled out, the magnetic field generating means are preferably arranged to provide the uniform field with its field direction in a vertical or, more preferably, substantially horizontal plane.

Viewed from a further aspect the invention also provides a method of magnetic resonance imaging of a sample exposed to a uniform magnetic field which has superimposed thereon a series of magnetic field gradients, characterised in that imaging is effected by electron spin resonance enhanced magnetic resonance imaging and in that said uniform field is the earth's ambient magnetic field or is an imposed magnetic field of not greater than 20 Gauss optionally combined with a magnetic field arranged to cancel out the earth's ambient field at the sample.

The method of generating a magnetic resonance image of a sample, conveniently a human or non-human animal body, conveniently comprises exposing said sample to a first radiation of a frequency selected to excite nuclear spin transitions in selected nuclei in said sample and to a second radiation of a frequency selected to excite electron spin transitions coupled to nuclear spin transitions of at least some of said nuclei and detecting free induction decay signals from said sample and generating therefrom a said image, the said first and second radiations being of frequencies selected to excite said transitions in the ambient magnetic field or other uniform magnetic field not greater than 20 Gauss.

In the method of the invention, the sample is exposed to the second radiation for at least part of each RF pulse sequence, e.g. during at least part of the period between the initial pulses of adjacent said sequences. Preferably exposure to the second radiation will be for some, the major part or all of the period during which no magnetic field gradient is imposed on the sample. Conveniently therefore the second radiation may be applied following FID signal determination in each pulse sequence.

A major factor in the concept of using the earth's magnetic field as the constant magnetic field required by the magnetic resonance imaging technique is that the enhancement using ESREMRI can be increased over the above theoretical limit of 330 if the magnetic field induced locally by hyperfine splitting in the esr electron transition, namely the hyperfine splitting constant expressed in Gauss, is much larger than the constant magnetic field. In fact, hyperfine splitting constants equivalent to 100-1000 G are known in some paramagnetic MRI contrast agents but these often have undesirable line widths. In a particularly preferred type of MRI contrast agent, namely the nitroxide stable free radicals, the electron transition is limited to a triplet which, in preferred contrast agents is relatively free from superhyperfine splitting and has a hyperfine splitting constant of about 20 G.

It can be shown that the contrast enhancement of the FID signal in ESREMRI is $$330(HSC+B_o)/B_o$$

where $B_o$ is the field strength of the uniform magnetic field (in Gauss) and HSC is the hyperfine splitting constant (also in Gauss).

The earth's magnetic field, while being locally extremely uniform, varies from place to place. However it is generally around 0.5 G. Using the above triplet with a hyperfine splitting constant at 20 G the theoretical maximum contrast enhancement is thus about $$\frac{330 \times 20.5}{0.5} = 13530$$

Thus, while the strength of the FID signal is related to the constant magnetic field strength and using the earth's field of 0.5 G instead of the 200 G normally used in ESREMRI, the signal strength can be expected to fall by a factor of about 400, the increased effect due to hyperfine splitting can reduce this fall by 20.5/0.5 to a factor of about 10. As explained below, other factors make such a reduction acceptable. If, in fact, a paramagnetic contrast agent is selected which has a suitable doublet or triplet with a coupling constant of 200 G or more, reduction in FID strength can even be avoided.

In general, the hyperfine splitting constant of the selected esr transition is preferably between 10 and 1000 G. While high values will give greater contrast enhancement, they are commonly associated with excessive line widths, thereby leading to excessive heating by the microwave radiation used.

Where the uniform magnetic field is generated by a magnet, this will still give substantial enhancement. Thus, for example, at a field strength of 5 G, using a paramagnetic substance with a hyperfine splitting constant of about 20 G, the maximum theoretical contrast enhancement will be increased by 25/5, i.e. 5 times, while the field strength has only been reduced 40 times as compared with a 200 G magnet.

Although there are great advantages in many circumstances in using the earth's field and dispensing completely with the magnetic means (e.g. a principal DC magnet) which generates the instrument's primary magnetic field, as indicated above the angle of declination of the earth's field may give difficulties in tomographic 'slicing' of the subject. Furthermore, from the manufacturer's point of view, it is preferable to provide apparatus tuned to a fixed DC field; the variation in the earth's field from place to place requires each apparatus to be adjustable in respect of the frequencies of the radiation and the receiving devices; the expense of this may well outweigh the cost of the very low field magnet which is contemplated. Where such a magnet is used, it will usually be desirable to balance the earth's field with suitable magnetic coils so that the direction of the uniform magnetic field is in an appropriate direction.

Where a magnet is used to generate the uniform field, the field strength may be up to 20 G but is more preferably 10 G or less, e.g. around 5 G. In general, magnets generating fields of adequate homogeineity may be built very economically at field strengths up to 10 G.

A major advantage of the earth's magnetic field is its great uniformity as compared with fields which can be produced by magnets in conventional MRI. The best m. gnets available produce fields having about 10 ppm inhomogeneity, while the inhomogeneity of the earth's field may be several orders lower. The decay time of the signal exciting the nuclear transition is greatly increased by the inhomogeneity of the field and moreover the improved homogeneity of the earth's field leads to a decreased $T_1$ of the order of 10-fold. Thus, the reduction in field strength of the FID signal, even when using an esr transition with a coupling constant of only 20 G, may be compensated by the increased decay times and shorter $T_1$ which enable more samples of the FID signal strength to be taken and a better and more accurate average value obtained. Furthermore, larger differences in $T_1$ and $T_2$ are observed at low field strengths giving better contrast between different tissues.

Furthermore, the gradient imposed on the constant magnetic field in order to generate tomographic 'slicing' has to be great enough to overcome inhomogeneity. If the spatial resolution provided by the gradient is about 2 mm, the fall in field strength over that distance must be significantly greater than the standard deviation of field strength values caused by inhomogeneity. Using the much more uniform earth's field, significantly lower fields can be used for the slicing gradient and, indeed for the other gradients used for the Fourier tranform technique. In normal MRI, the slicing gradient is commonly of the order of 0.5 G/cm whereas using the earth's field a gradient in the range 0.01 to 0.20 G/cm, e.g. about 0.05 G/cm can be used.

The same advantages are obtained using magnets to generate fields up to 20 G. Such fields can be made relatively uniform in terms of percentage inhomogeneity and it is the absolute values of local inhomogeneities which affect decay time and $T_1$. The inhomogeneities will be of low strength because the field itself is of low strength and may be comparable to those of the earth's field.

It should be noted that the esr exciting frequency used will be that appropriate to the earth's magnetic field or other low fields up to 20 G rather than the 200 G fields normally used in ESREMRI. It will be appreciated that the gradient field is not relevant since it is not applied during the esr excitation pulses. If the hyperfine splitting constant is 20 G, the effective magnetic field acting on the unpaired electron in the earth's field is 20.5 G and since the precession frequency of the electron is 2.8 MHz/G, the total precession frequency is $2.8 \times 20.5$ MHz, that is about 57 MHz. Similar calculations give the MW frequency in other fields up to 20 G. The line width of the esr spectrum is of the order of 1 MHz so that the esr exciting frequency should be within 1 MHz of the frequency giving maximum resonance in the magnetic field of the electron. If necessary, the latter can be determined precisely by experiment.

With regard to the frequency exciting the nuclear transitions, 2 kHz gives adequate resonance for proton transitions in the applied magnetic field, which will be the sum of the earth's field and the field of the slicing gradient.

Generally in the apparatus of the invention the first radiation source will preferably be capable of emitting radiation of frequency 1-50 kHz, especially 1.5-20 kHz, particularly 2-15 kHz for $^1$H ESREMRI. The second radiation source will preferably be capable of emitting radiation in the range 20-1000 MHz, especially 50-200 MHz, particularly preferably about 100 MHz.

With the use of lower second radiation frequencies than those required for ESREMRI at conventional or low primary magnetic field strengths, frequencies of about 100 MHz for example, the new imaging technique offers a major advantage over conventional ESREMRI since the absorption of the second radiation by the human or animal body is much reduced and thus the subject being imaged can receive significantly higher second radiation intensities and exposures without experiencing unacceptable heating. Since, as is shown by the results presented in EP-A-296833, FID intensity and the contrast effect increases with increasing intensity of the second radiation, the ability to utilise higher "MW"

power will enable MR images to be detected with better S/N ratios and/or with shorter image acquisition times.

The magnetic resonance image of the sample can be generated in the conventional manner from the detected FID signals. In particular it is not necessary to detect comparative signals from the sample while this is not exposed to the second radiation. Thus generally the apparatus of the invention will comprise means, generally a computer, for transforming the detected FID signals into MR images, these means being arranged to generate such images using only signals detected following emission of both first and second radiations by the radiation sources. If desired, the ESREMRI apparatus of the present invention may of course include a magnet means energisable to generate a primary magnetic field so that the apparatus may when desired operate as a conventional ESREMRI apparatus or as a conventional MRI apparatus.

In general, at ambient magnetic field the frequencies required to excite the nuclear and electron spin transitions will be significantly lower than those required at the primary magnetic field strengths conventionally employed in MRI and ESREMRI and in ESR and NMR spectroscopy. However, since nuclear magnetic resonance stimulating radiation and electron spin resonance stimulating radiation are conventionally referred to as radiofrequency (RF) and microwave (MW) radiations respectively the first and second radiations generated by the first and second radiation sources in the apparatus of the invention will for the sake of convenience be referred to hereinafter as "RF" and "MW" radiations. It must be appreciated that the first and second radiations may in fact lie at frequencies outside the ranges conventionally understood as being RF and MW frequencies and especially may be of lower frequencies than those conventionally considered to be RF or MW.

In conventional nmr spectroscopy, it has long been known that if a sample comprising a paramagnetic species and a species containing non-zero spin nuclei, for example sodium dissolved in ammonia, is placed in a strong magnetic field and an esr transition of the paramagnetic species (sodium) is saturated, then peaks in the nmr spectrum of the other species can be very strongly enhanced due to coupling between the electron and nuclear spin transitions. The effect has been termed the Overhauser effect, or dynamic nuclear polarization, as exciting the esr transition drives a nuclear spin system at equilibrium towards a new equilibrium distribution with a relatively higher excited state population. In the present invention, this effect is operated not as in conventional spectroscopy to generate a strong peak in an nmr spectrum but instead to amplify population difference due to relaxation of an excited nuclear spin system.

Where only a portion of the nuclei whose spin transitions produce the FID signal (hereinafter the "resonating nuclei") couple with the unpaired electrons of the paramagnetic species, for example due to low concentration or non-uniform distribution of the paramagnetic species in the volume being imaged, the operation of the method and apparatus of the invention will also result in contrast enhancement in the image—thus the FID signal from the resonating nuclei coupling with the unpaired electrons will be enhanced relative to the signals from the non-coupling nuclei. Where the paramagnetic species is either naturally abundant in specific tissues only or is administered in a contrast medium so as to congregate in such tissues, the operation of the invention will therefore allow generation of images in which the contrast enhancement of these tissues is high. It should be noted however that where the power level of the second radiation or the concentration of the paramagnetic material is particularly low it is possible for MR image intensity to be reduced rather than enhanced. Even in such cases however the modified contrast achieved in the resulting MR images may be of interest.

As mentioned above, the paramagnetic substance possessing the esr transition which couples with the nmr transition of the resonating nuclei may be naturally present within the sample or more preferably may be administered thereto in a contrast medium. Coupling with the resonating nuclei may be either scalar coupling with resonating nuclei within the same molecules as the unpaired electrons or dipolar coupling with resonating nuclei, generally water protons in the body fluids, in molecules in the environment of the paramagnetic centres.

Electron spin systems do occur naturally in the body, e.g. in substances synthesized in certain metabolic pathways such as the oxidation chain in the cell mitochondria.

Insofar as administered contrast agents are concerned however, in one embodiment of the invention there may be used a contrast medium which contains both the resonating nuclei and the substance possessing the desired electron spin transition, and in a further embodiment the substance possessing the desired electron spin transition may itself also contain one or more of the resonating nuclei. This is especially preferred where the resonating nuclei are rarely abundant in the sample being imaged, for example where the resonating nuclei are $^{13}C$ or $^{19}F$ nuclei where scalar coupling will be important in the amplified FID. Using such a contrast agent, the FID signal will derive predominantly from body sites containing the contrast agent thereby facilitating imaging of specific tissues or organs.

Alternatively, and generally more preferably, the contrast agent may contain a paramagnetic centre which undergoes dipolar coupling with resonating nuclei naturally occurring in the sample, e.g. in body tissue or more specifically with resonating protons in water molecules in the sample.

In the method of the invention, selection of the esr system which couples with the resonating nuclei is important. In a particularly preferred embodiment of the invention the paramagnetic material will be selected from amongst those materials for which the esr spectrum of the unpaired electron comprises a multiplet (i.e. two or more, preferably 2–10, especially preferably 3–5, peaks) or a broad peak.

Using such a paramagnetic contrast agent the second radiation will preferably be set to excite a high field portion of the esr spectrum, e.g. a high field line in a multiplet or a band of a broad esr peak to the high field side of peak centre.

To ensure that a high contrast effect is achieved using the apparatus and method of the invention, the excitation of the esr transition of the paramagnetic material should be as great as possible.

Since the linewidths of esr transitions in the esr spectrum are proportional to $T_{2e}^{-1}$, the bandwidth required for the second radiation that is used to excite the esr transition will be smaller where the transition corresponds to a narrow line in the esr spectrum and a long transverse relaxation time is therefore desirable.

Particularly preferably, the substance possessing the esr transition excited by the second radiation will be a paramagnetic material whose esr spectrum consists of a set of narrow lines (for example resulting from hyperfine splitting of a single transition under the effect of neighbouring non-zero spin nuclei within the structure of the paramagnetic substance). Where the esr spectrum contains a reasonably small number of lines it will, as discussed below, be possible simultaneously to excite several or all of the corresponding transitions.

Conventional paramagnetic MRI contrast agents, such as the gadolinium compounds (e.g. Gd-DTPA) suggested by Schering (EP-A-71564), have large spectral linewidths and would not generally be selected since they are highly likely to require unduly large "MW" power levels in order to achieve any significant amplification of the FID signal. Generally therefore where a contrast agent is to be used as the source of the esr transition, it should preferably have a stimulable esr transition having a line width (i.e. full width at half maximum in the absorbtion spectrum) of the order of 1–5 Gauss or less, preferably 100 milliGauss or less, and especially preferably 50 milliGauss or less. If the esr spectrum contains a plurality of lines it is furthermore preferred that the total number of these lines be small, for example 2–10, preferably 2 or 3, and that the separation of the high field line from the multiplet centre should be as large as possible, e.g. greater than 2 G, preferably greater than 10 G, especially preferably greater that 15 G (or the frequency equivalent thereof) at ambient magnetic field.

Where the esr spectrum of the paramagnetic material at ambient field is a multiplet, or is a broad peak, then the contrast effect can be enhanced by the use of broadband "MW" radiation or by the use of "MW" radiation of two or more central frequencies to excite several or all of the esr transitions or to enhance the efficiency of excitation.

As with the resonating nuclei, the Larmor frequency of the unpaired electron coupling with the resonating nuclei is also dependent on the local magnetic field and not only will the esr transition have a finite linewidth in the esr spectrum, but that spectrum will generally also show some fine structure, i.e. splitting due to the fields generated by non-zero spin nuclei in the paramagnetic material.

In general, the paramagnetic material will most desirably be a molecule or complex containing few non-zero spin muclei or few non-zero spin nuclei at positions where they would cause any unpaired electrons. Conveniently, the molecule may have the atoms near to the paramagnetic centre predominantly selected from zero nuclear spin isotopes or from elements for which the natural abundance of non-zero spin nuclear isotopes is low. Such selection may include elements in which the natural abundance of spin=½ nuclei is low and isotopes such as $^{12}C$, $^{2}H$, $^{32}S$, $^{14}Si$ and $^{16}O$ may for example be used to build up the molecular structure adjacent to the location of the unpaired electron.

While the use of compounds, salts or chelates or other complexes of certain paramagnetic metal species may be contemplated, such materials will only be of particular interest where the esr linewidth is of the order of or less than about 1 Gauss. Thus the use of physiologically tolerable copper chelates may for example be contemplated.

Nonetheless physiologically tolerable stable free radicals are of particular interest for use as the paramagnetic material.

One particularly interesting group of stable free radicals are the nitroxide stable free radicals of which many have been suggested in the literature for use as spin labels or as paramagnetic contrast agents for conventional MRI. Moreover, several of these compounds are readily available commercially, for example from Aldrich. The nitroxide stable free radicals are of particular interest as their toxicities and pharmacokinetics have been studied and show the compounds to be suitable for in vivo MRI and as the esr linewidths, especially for compounds in which the atoms adjacent to the NO moiety are fully substituted (i.e. carry no protons), are adequately small at the concentrations required to give contrast enhancement.

A further particularly interesting group of stable free radicals for use according to the invention are the deuterated nitroxide stable free radicals of which several have been suggested in the literature for use as spin labels. Certain of these compounds are readily available commercially, for example from Merck Sharpe & Dohme. Where the stable free radicals are only partially deuterated, it is especially preferred that the hydrogens at those sites where $^1H$ would cause the greatest, or indeed any significant, reduction in the $T_{1e}$ or $T_{2e}$ values for the unpaired electron should be $^2H$.

The deuterated radicals used according to the invention preferably have deuterium atoms in place of protons within 3, preferably 4 and especially preferably 5 or more, bonds of the paramagnetic centre, e.g. the oxygen of an NO moiety. More especially the radicals are preferably perdeuterated; however where radicals contain labile hydrogens, e.g. acid, amine or alcohol hydrogens, these may preferably be $^1H$ and compounds containing hydrogens distant from the paramagnetic centre which are $^1H$ may also be used to advantage.

As nitroxide stable free radicals, or deuterated nitroxide stable free radicals, there may conveniently be used cyclic nitroxides wherein the NO moiety occurs in a 5 to 7-membered saturated or ethylenically unsaturated ring with the ring positions adjacent to it being occupied by doubly saturated carbon atoms and with one of the remaining ring positions being occupied by a carbon, oxygen or sulphur atom and the remaining ring positions being occupied by carbon atoms. Alternatively there may be used as the optionally deuterated nitroxide stable free radicals compounds in which the NO moiety occurs in a chain where the adjacent chain atoms are carbon and are not bound to any protons.

Preferred nitroxides may be represented by the formula (I)

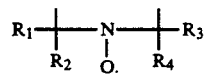

(I)

wherein $R_1$ to $R_4$ may represent deuterium or lower (for example $C_{1-4}$) alkyl or hydroxyalkyl groups and $R_1$ may also represent carboxy substituted $C_{1-10}$ alkyl groups and $R_2$ may also represent a higher (e.g. $C_{5-20}$) alkyl group or a carboxy substituted $C_{1-20}$ alkyl group, or $R_1$ and $R_3$ may together represent an alkylene or alkenylene group, e.g. having up to 4, especially preferably up to 3, carbon atoms and X represents an optionally substituted, saturated or ethylenically unsaturated bridging group having 2 to 4 atoms in the backbone of the bridge one of the backbone atoms being carbon, oxygen or sulphur and the remaining backbone atoms being carbon, preferably with one or more of $R_1$ to $R_4$ and X comprising at least one deuterium, especially preferably any carbon-bound hydrogen within three, and especially preferably within 4, bonds of the nitroxyl nitrogen being a deuterium atom.

In formula I, the moieties $CR_1R_2$ and $CR_3R_4$ are preferably the same. Particularly preferably, $R_1$ to $R_4$ are the same, and it is especially preferred that $R_1$ and $R_4$ should all be perdeuterated methyl groups.

In formula I the optional substitution on X, which preferably is an optionally mono-unsaturated $C_{2-3}$ chain, may for example take the form of halogen atoms or oxo, amino, carboxyl, hydroxy or alkyl groups or combinations or derivatives thereof such as for example amide, ester, ether or N-attached heterocyclic, e.g. 2,5-dioxopyrrolidino, groups. Many examples of substituted X groups are described in the literature mentioned below.

The nitroxide molecule may if desired be bound to a further substance, such as for example a sugar, polysaccharide, protein or lipid or to other biomolecules, for example to enhance the blood pooling effect or the tissue- or organ- targetting ability of the nitroxide stable free radical.

In the method and use of the invention there may particularly conveniently be used the nitroxide stable free radicals described in EP-A-296833 and in our copending British patent application no. 8817137.

In a still further aspect the invention also provides the use of a physiologically tolerable paramagnetic material, e.g. a stable free radical, for the manufacture of a contrast medium for use in a method of diagnosis of a human or non-human animal, preferably mammalian, body involving imaging using the method of the invention.

It will be appreciated that where references are made herein to the limits for esr linewidths these will be the linewidths at imaging conditions, e.g. at the imaged sites. Particularly preferably however the linewidth criteria will be satisfied at the local concentration limits mentioned below.

The contrast medium may contain, besides the paramagnetic material, formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external escape ducts (such as the digestive tract, the bladder and the uterus), or for injection or infusion into the cardiovascular system. However, solutions, suspensions and dispersions in physiologically tolerable media will generally be preferred.

For use in in vivo diagnostic imaging, the contrast medium, which preferably will be substantially isotonic, may conveniently be administered at a concentration sufficient to yield a 1 micromolar to 10 mM concentration of the paramagnetic substance at the image zone; however the precise concentration and dosage will of course depend upon a range of factors such as toxicity, the organ targetting ability of the contrast agent, and administration route. The optimum concentration for the paramagnetic substance represents a balance between various factors. In general concentrations may lie in the range 0.1 to 100 mM, especially 1 to 10 mM, more especially 2 to 5 mM. Compositions for intravenous administration preferably will contain the paramagnetic material at concentrations of 10 to 1000 mM, especially preferably 50 to 500 mM. For ionic materials the concentration will particularly preferably be in the range 50–200 mM, especially 140 to 160 mM and for non-ionic materials 200–400 mM, especially 290–330 mM. For imaging of the urinary tract or the renal system however compositions may perhaps be used having concentrations of for example 10 100 mM for ionic or 20 to 200 mM for non-ionic materials. Moreover for bolus injection, the concentration may conveniently be 0.1 to 100 mM, preferably 5 to 25 mM, and especially preferably 6–15 mM.

The nitroxides in the contrast medium of the invention will preferably exhibit esr linewidths of less than 1 Gauss, especially preferably less than 100 mG, at concentrations of up to 10 mM, especially at 1 or 2 mM.

As mentioned above, the first and second radiations are "RF" and "MW" respectively and the first and second radiation sources will thus be sources capable of emitting radiation of the appropriate frequencies.

The first radiation source is preferably provided with means for adjusting the pulse timing and duration so that the desired imaging technique (e.g. SR, IR, SE, FI, etc.) may be chosen and so that the pulse sequence repetition rate 1/TR may be selected to increase or reduce image acquisition time or to determine $T_1$, $T_2$ or nuclear (usually proton) density.

The first radiation source is also preferably provided with means for adjusting the central frequency, bandwidth, and intensity of the first radiation pulses.

As in conventional MRI, the pulses of the first radiation may be applied while the sample is in a magnetic field which is the combination of a uniform magnetic field and an imposed magnetic field gradient in one direction (the Z direction). Unlike conventional MRI or ESREMRI however the uniform magnetic field need not be generated by a primary magnet but may be the earth's ambient field. The central frequency and bandwidth of the nuclei exciting pulse together with the Z direction field gradient during the exciting pulse serve to define the position along the Z axis and the thickness in the Z direction of the slice perpendicular to the Z axis containing nuclei whose spin transitions are excited by that pulse. Thus, for example, Fourier transformation of a square wave pulse of central frequency $V_0$ would show such a pulse to contain a range of frequencies centered about $V_0$ and each corresponding to the Larmor frequency of resonating nuclei in a particular XY plane along the Z axis. Thus by providing the apparatus with means for adjusting or selecting the central frequency and bandwidth of the first radiation, the section through the sample (the image zone) and of course the isotopic nature and chemical environment of the resonating nuclei may be selected.

The second radiation source may be a continuous wave (CW) transmitter or alternatively may be arranged to emit pulses or trains of pulses of the second radiation.

To achieve full benefit of the amplified FID signal of the nuclear spin system and to minimize the dosage of the contrast agent (if required), it is therefore beneficial to excite and preferably saturate the electron spin system using a range of frequencies matched to the frequencies of all or most of the peaks in the esr spectrum. This can be done by use of a second radiation source emitting a band of frequencies (e.g. in pulse trains) or by use of two or more sources emitting at different frequencies.

To achieve the desired frequency spread in the second radiation, it may be desirable to use pulses of relatively short duration (hereinafter "micropulses"), for example of the order of nano or microseconds, and to optimize the amplified population difference of the nuclear spin system by keeping the esr transition at or near saturation it may thus be desirable to arrange the second radiation source to emit a train of micropulses, the adjacent micropulses being so spaced as not to permit serious longitudinal relaxation of the electron spin system in the periods between the micropulses.

Alternatively, by providing a decoupling means comprising a third radiation source capable of exciting spin transitions in certain nuclei (other than the resonating nuclei) the number of peaks in the esr spectrum or the linewidth of a broad peak may be reduced. Thus multiple peaks in the esr spectrum of the unpaired electron can arise from coupling between the spins of the electron and nearby non-zero spin nuclei (the transition splitting nuclei) in the same molecule. Where the transition splitting nuclei are not the resonating nuclei for the MRI procedure (for example where they are of different isotopic nature or, if they are of the same isotopic nature, where their chemical shifts are such that their Larmor frequencies are sufficiently distant from that of the resonating nuclei in the same region that they are not excited by the first radiation), the spins of the unpaired electrons and the transition splitting nuclei can be decoupled by irradiating the nmr transition of the transition splitting nuclei with a high intensity radiation at the Larmor frequency of the transition splitting nuclei. With such irradiation, the hyperfine structure in the esr spectrum can be reduced. For the purposes of the present invention however, where the esr spectrum is a multiplet or a broad peak decoupling will only be desirable to the extent that the resulting esr spectrum still fulfills the selection criteria mentioned above, namely that at least one multiplet having a hyperfine splitting constant between 10 and 1000 is retained. Where decoupling is to be effected the ESREMRI apparatus should also be provided with means for emitting the third radiation. The third radiation emission may be continuous or pulsed (or may take form of a continuous train on a series of trains of micropulses as described earlier for the second radiation) and suitably is emitted over substantially the same period as the second radiation.

The second radiation source(s) and, where present, the third radiation source will therefore, like the first radiation source, preferably be provided with means for adjusting pulse timing, pulse duration, central frequency, bandwidth and intensity if they are pulsed sources, and central frequency, bandwidth and intensity if they are CW emitters.

The sample may be exposed to the second radiation either continuously or for one or more periods between the initiating pulses of subsequent first radiation pulse sequences. Preferably, exposure to the second radiation will be in the period in which no field gradients are imposed on the sample, e.g. for at least part, and preferably all, of the delay period between the final FID signal detection period of each sequence and the initial first radiation pulse of the next.

The ESREMRI apparatus should particularly preferably be arranged for operation with amplified FID and with or without imposition of a uniform field generated by a primary magnet. The magnet may be a low field magnet e.g. up to 20 G. However, it may be convenient to use a conventional apparatus equipped with a more powerful magnet which is either not used or used at low field strength.

Where the earth's field is not to be used as the uniform field, means will be provided, for example suitable Helmholtz coils, to exactly balance the ambient field, leaving the magnetically generated low strength field as the sole uniform field.

The apparatus is arranged to allow ESREMRI of the sample to be performed and may simply constitute an MRI apparatus of conventional type adapted by the provision of radiation sources capable of emitting radiation of the appropriate "MW" and "RF" frequencies and optionally by provision of the magnetic field generating means discussed above.

The MRI procedure involved in the new method of ESREMRI may also involve any one of the conventional image generation procedures, such as for example back projection or three- or two-dimensional Fourier transformation (3DFT and 2DFT), although the latter two of these may generally be preferred.

For 2DFT, a small field gradient (the slice selection gradient) is applied, e.g. in the Z direction and the sample is exposed to an RF pulse (the initiating pulse) of a given central frequency, bandwidth and duration. Together, the central frequency, the bandwidth and the combination of the ambient field and the slice selection gradient serve to define the position and thickness of the image zone, the tomographic section through ,the sample transverse to the slice selection gradient in which the resonating nuclei will be excited by the RF pulse. The duration of the pulse determines the resultant change in transverse and longitudinal magnetization of the resonating nuclei. With a 90° pulse, after the slice selection gradient and the "RF" pulse are simultaneously terminated, a small field gradient (the phase encoding gradient) is then imposed for a short period in a direction transverse to the slice selection gradient, e.g. in the Y direction, causing the phase of the oscillating FID signal to become dependant on the position in the Y direction of the signal's source and thus encoding spatial information in the phase of the FID signal. After the phase encoding gradient is terminated, a third small field gradient (the read gradient) in a direction perpendicular to the previous two (the X direction) is imposed to encode spatial information in the FID frequency and the FID signal is detected and its intensity as a function of time is recorded during the imposition of the read gradient.

The FID signal that is detected is the combination of signals from resonating nuclei throughout the image zone. If in simple terms it is viewed as the sum of signals from an array of sources extending in the XY plane, the oscillating signal from each source will have an overall intensity dependent on the local density of the resonating nuclei, a frequency dependant on the position of the source in the X direction and a phase dependant on the position of the source in the Y direction. signal decays and, after a delay time to permit equilibration, the slice selection gradient is reimposed and the initiating RF pulse of the subsequent pulse sequence is applied.

Image generation requires detections of the FID signal for a series of pulse sequences, each with a phase encoding gradient of different strength or duration, and two-dimensional Fourier transformation of the resultant data can extract the spatial information to construct a two dimensional image, in the case described an SR image.

Different imaging techniques, such as IR, SE, etc., or different image generation techniques, e.g. simultaneous slice, volume acquisition, back projection etc., will of course require different pulse and field gradient imposition sequences, sequences which are conventional in the art.

The invention will now be described further by way of example and with reference to the accompanying drawings, in which:

FIG. 2 is a schematic perspective drawing of the emitters of the first and second radiation in the apparatus of FIG. 1.

Figure 1:
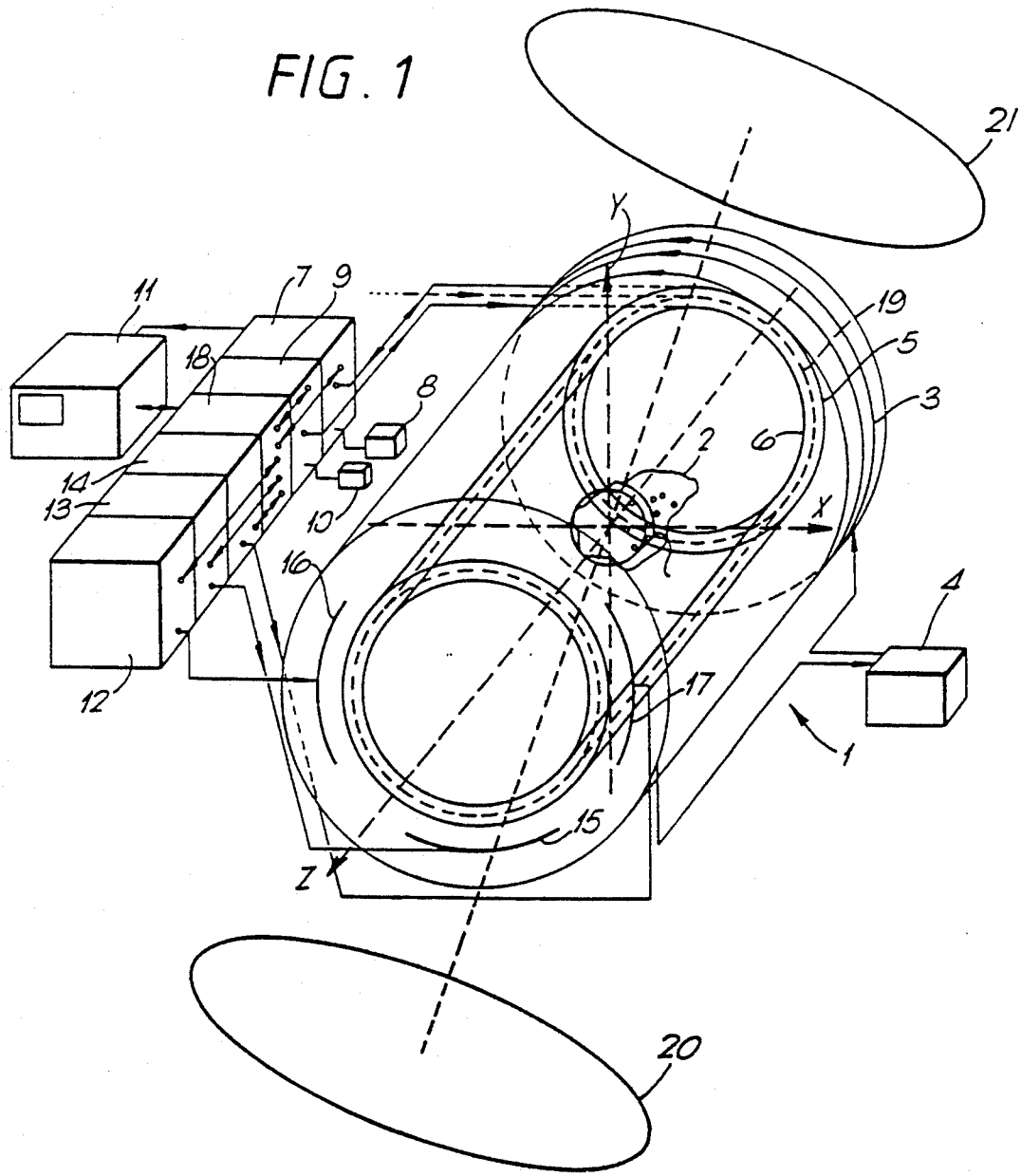
FIG. 1 is a schematic perspective drawing of an ESREMRI apparatus according to the invention.

Referring to FIG. 1, there is shown an ESREMRI apparatus 1 having a sample 2, dosed with a paramagnetic contrast medium manufactured according to the invention, placed at the axis of the coils of a low field electromagnet 3. Power from DC supply 4 to the electromagnet 3 enables a small primary magnetic field to be generated if the ambient field is not to be the sole uniform magnetic field. Where the magnet 3 is to be used, coils 20 and 21 will be so placed and energised as exactly to balance the earth's magnetic field.

The apparatus is further provided with resonators 5 and 6 for emitting the first and second radiations respectively. Resonator 5 is connected to "RF" transceiver 7 powered by power supply 8 and resonator 6 is connected, for example by waveguides, to "MW" generator 9 which is powered by power supply 10.

"MW" generator 9 may be arranged to emit "MW" radiation having more than one maximum frequency in order to excite more than one esr transition.

The frequency selection, bandwidth, pulse duration and pulse timing of the first and second radiations emitted by resonators 5 and 6 are controlled by control computer 11 and interface module 18 which also optionally control the energisation or deenergisation of electromagnet 3.

Computer 11 also controls the power supply from power sources 12, 13 and 14 to the three pairs of Helmholtz coils 15, 16 and 17 which are shown in further detail in FIG. 2. The coils of coil pair 15 are coaxial with the coils of electromagnet 3 and the saddle coils of coil pairs 16 and 17 are arranged symmetrically about that axis, the Z axis, with their own axes mutually perpendicular and perpendicular to the Z axis. Coil pairs 15, 16 and 17 are used to generate the magnetic field gradients that are superimposed on the ambient field at various stages of the imaging procedure, e.g. in two-dimensional Fourier transform imaging, and the timing sequence for operation of the coil pairs and for operation of the "MW" generator and the "RF" transceiver is controlled by computer 11 and interface module 18.

The apparatus may also be provided with decoupler comprising a further "RF" resonator 19 (shown with broken lines) connected to an "RF" transmitter and a power supply (not shown) and controlled by computer 11. The decoupler may be operated to emit a third radiation at a frequency selected excite the nuclear spin transition in non-zero spin nuclei in the contrast agent.

In operation using only the ambient field the power supply to electromagnet 3 is switched off, the sample 2, e.g. a patient, is placed within the coil cavity and the imaging procedure is begun. Where electromagnet 3 is to be used it is switched on and in general will remain energised throughout. Coils 20 and 21 to balance the ambient field are also energised. Such coils may be of large diameter and even surround the apparatus as shown or the room in which the apparatus is located.

Interface module 18 activates the power supply to coil pair 15 for a short time period during which DC current flowing through the coils of coil pair 15 in opposite directions about the Z axis results in an approximately linear field gradient in the Z direction being imposed on the ambient field.

Within the time period for which coil pair 15 is energized, interface module 18 activates "RF" transceiver 7 to cause resonator 5 to emit an "RF" pulse, e.g. a 90° pulse, to excite the nmr transition of those resonating nuclei (generally protons) whose Larmor frequencies correspond to the frequency band of the "RF" pulse. The duration, intensity, band width and central frequency of the "RF" pulse may be selected by computer 11.

Effectively the "RF" pulse serves to excite the MR transition of the selected non-zero nuclear spin isotope (generally water protons) within a cross-section (the image zone) of the sample that is transverse to but has thickness in the Z direction.

On termination of the "RF" pulse, current in coil pair 15 is also terminated and after a very short delay interface module 18 energizes coil pair 16 to provide a field gradient in the Y direction for a short time period. This is termed the phase encoding gradient as the field gradient causes the Larmor frequency for the resonating nuclei to vary linearly across the image zone in the Y direction for the period that coil pair 15 is energized. With the removal of the perturbation of the Larmor frequencies on termination of the phase encoding gradient, the oscillation frequencies of the contributions to the FID signal from different source areas of the image zone return to being substantially the same, but the phases of such contributions are shifted to an extent dependant on the location of the particular source area along the Y direction.

After terminating current in coil pair 16, the interface module 18 then energizes coil pair 17 to provide a field gradient (the read gradient) in the X direction, and reactivates "RF" transceiver 7 to detect the FID signal from the sample.

The FID signal is assumed to arise from the transverse magnetization of the nuclear spin system within the image zone since the MR transition was excited by the "RF" pulse for resonating nuclei in this zone only. As described above, the intensity of the FID signal as a function of time contains encoded information regarding the distribution of the resonating nuclei in the image zone in the X and Y directions respectively.

The FID signal intensity falls off exponentially with time as the system dephases and the period for which the read gradient is imposed and the transceiver 7 detects the FID signal from the sample is generally very short, for example of the order of milliseconds.

To generate an MR image of the image zone it is necessary to repeat the pulse and detection sequence for many further times, e.g. 64–1024 times, each time generating phase encoding gradients of different magnitude or duration. Often, to produce a good S/N ratio, signals for several, e.g. 2–4, identically performed sequences will be summed. FID signals for each set of sequences are transformed by the computer 11 using a standard two-dimensional Fourier transform algorithm to produce the desired spatial images of the image zone.

In conventional MRI, after termination of the only or the last FID signal detection period in a pulse and detection sequence and before the subsequent imposition of the slice selection gradient and emission of the initiating RF pulse of the next sequence, it has been necessary to wait for a delay period, generally of the order of seconds, until the resonating nuclei have relaxed to near equilibrium in order to build up sufficient longitudinal magnetization for the FID signal following the new RF pulse to be sufficiently strong to give an acceptable S/N ratio.

However, in ESREMRI, the delay period following the only or the last detection period may be reduced by the use of the amplified nuclear population difference resulting from the coupling between the electron MR and nuclear MR transitions. Alternatively put, the sample may be irradiated with "MW" radiation at the beginning of the or each "RF" pulse sequence to build up the enhanced nuclear population difference. Thus, for example at least in a period between termination of the last read gradient for each pulse sequence and the emission of the initiating "RF" pulse of the next sequence, for example for a period of about 10 ms to 100 ms, interface module 18 activates "MW" generator 9 to cause the sample to be irradiated with "MW" radiation of a central frequency corresponding to the Larmor frequency of the paramagnetic centre in the contrast agent in the sample, either CW radiation or, preferably, a train of radiation pulses.

To minimise field inhomogeneities, the sample cavity of the apparatus of the invention should preferably be provided with shielding (not shown) between coils 15, 16 and 17 and the electronic control equipment and power sources (4, 7-14, 18).

In view of the reduced FID signal strengths to be received, it may be desirable to reduce the signal noise by cooling the electronic equipment of the ESREMRI apparatus.

I claim:

1. A method of magnetic resonance imaging of a sample exposed to a uniform magnetic field which has superimposed thereon a series of magnetic field gradients, characterised in that imaging is effected by electron spin resonance enhanced magnetic resonance imaging and in that said uniform field is the earth's ambient magnetic field.

2. A method as claimed claim 1 comprising exposing said sample to a first radiation of a frequency selected to excite nuclear spin transitions in selected nuclei in said sample and to a second radiation of a frequency selected to excite electron spin transitions coupled to nuclear spin transitions of at least some of said nuclei and detecting magnetic resonance signals from said sample and generating therefrom a said image.

3. A method as claimed in claim 2 wherein there is introduced into said sample a paramagnetic contrast agent having in its esr spectrum a transition excitable by said second radiation.

4. A method as claimed in claim 3 wherein said transition forms part of a multiplet in said spectrum.

5. A method as claimed in claim 4 wherein the separation of said transition from the centre of said multiplet is at least 2 gauss at said uniform field.

6. A method as claimed in claim 4 wherein the hyperfine coupling constant of said transition is 10 to 1000 gauss.

7. A method as claimed in claim 4 wherein said transition is a broad peak in said spectrum.

8. A method as claimed in claim 3 wherein said transition has a linewidth of less than 1 gauss.

9. A method as claimed in claim 3 wherein said contrast agent is a physiologically tolerable stable free radical.

10. A method as claimed in claim 9 wherein said contrast agent is a nitroxide stable free radical.

11. Electron spin resonance enhanced magnetic resonance imaging apparatus having a first radiation source capable of emitting a first radiation of a frequency selected to excite nuclear spin transitions in selected nuclei in a sample being imaged, a second radiation source capable of emitting a second radiation of a frequency selected to excite electron spin transitions coupled to the nuclear spin transitions of at least some of said selected nuclei, means for exposing said sample to a magnetic field gradient imposed on a uniform magnetic field and means for detecting magnetic resonance signals from said selected nuclei during the imposition of a said magnetic field gradient, characterised in that said first and second radiation sources are arranged to emit radiations of frequencies selected to excite said transitions using as the uniform magnetic field the earth's ambient magnetic field.

12. Electron spin resonance enhanced magnetic resonance imaging apparatus having a first radiation source capable of emitting a first radiation of a frequency selected to excite nuclear spin transitions in selected nuclei in a sample being imaged, a second radiation source capable of emitting a second radiation of a frequency selected to excite electron spin transitions coupled to the nuclear spin transitions of at least some of said selected nuclei, means for exposing said sample to a magnetic field gradient imposed on a uniform magnetic field and means for detecting magnetic resonance signals from said selected nuclei during the imposition of a said magnetic field gradient, characterised in that said first and second radiation sources are arranged to emit radiations of frequencies selected to excite said transitions using as the uniform magnetic field a magnetic field being a uniform field not greater than 20 Gauss combined with a field exactly balancing the earth's magnetic field.

13. Apparatus as claimed in claim 12 wherein said means for generating a uniform magnetic field are arranged to generate a said uniform magnetic field of 10 Gauss or less.

14. Apparatus as claimed in claim 11 wherein said first radiation source is arranged to emit radiation of frequency 1 to 50 kHz and said second radiation source is arranged to emit radiation of frequency 20 to 1000 MHz.

15. A method of magnetic resonance imaging of a sample exposed to a uniform magnetic field which has superimposed thereon a series of magnetic field gradients, characterised in that imaging is effected by electron spin resonance enhanced magnetic resonance imaging and in that said uniform field is an imposed magnetic field of not greater than 20 Gauss combined with a magnetic field so imposed as to cancel out the earth's ambient field at the sample.

16. A method as claimed in claim 14 comprising exposing said sample to a first radiation of a frequency selected to excite nuclear spin transitions in selected nuclei in said sample and to a second radiation of a frequency selected to excite electron spin transitions coupled to nuclear spin transitions of at least some of said nuclei and detecting magnetic resonance signals from said sample and generating therefrom a said image.

17. A method as claimed in claim 16 wherein there is introduced into said sample a paramagnetic contrast agent having in its esr spectrum a transition excitable by said second radiation.

18. A method as claimed in claim 17 wherein said transition forms part of a multiplet in said spectrum.

19. A method as claimed in claim 18 wherein the separation of said transition from the centre of said multiplet is at least 2 Gauss at said uniform field.

20. A method as claimed in claim 18 wherein the hyperfine coupling constant of said transition is 10 to 1000 Gauss.

21. A method as claimed in claim 18 where said transition is a broad peak in said spectrum.

22. A method as claimed in claim 17 wherein said transition has a linewidth of less than 1 Gauss.

23. A method as claimed in claim 17 wherein said contrast agent is a physiologically tolerable stable free radical.

24. A method as claimed in claim 23 wherein said contrast agent is a nitroxide stable free radical.

25. A method as claimed in claim 15 wherein said first radiation source is arranged to emit radiation of frequency 1 to 50 kHz and said second radiation source is arranged to emit radiation of frequency 20 to 1000 MHz.

* * * * *